US009470639B1

(12) United States Patent
Zhuang et al.

(10) Patent No.: US 9,470,639 B1
(45) Date of Patent: Oct. 18, 2016

(54) OPTICAL METROLOGY WITH REDUCED SENSITIVITY TO GRATING ANOMALIES

(71) Applicant: KLA-Tencor Corporation, Milpitas, CA (US)

(72) Inventors: Guorong V. Zhuang, San Jose, CA (US); Shankar Krishnan, Santa Clara, CA (US); Lanhua Wei, Fremont, CA (US); Walter Mieher, Los Gatos, CA (US); Paul Aoyagi, Sunnyvale, CA (US)

(73) Assignee: KLA-Tencor Corporation, Milipitas, CA (US)

( * ) Notice: Subject to any disclaimer, the term of this patent is extended or adjusted under 35 U.S.C. 154(b) by 0 days.

(21) Appl. No.: 15/014,987

(22) Filed: Feb. 3, 2016

Related U.S. Application Data

(60) Provisional application No. 62/111,421, filed on Feb. 3, 2015.

(51) Int. Cl.
*G01J 4/00* (2006.01)
*G01N 21/95* (2006.01)
(Continued)

(52) U.S. Cl.
CPC ......... *G01N 21/9501* (2013.01); *G01N 21/211* (2013.01); *G01N 21/255* (2013.01); *G01N 2021/213* (2013.01); *G01N 2201/0683* (2013.01); *G01N 2201/06113* (2013.01); *G01N 2201/12* (2013.01)

(58) Field of Classification Search
CPC ............... G01N 21/211; G01N 21/21; G01N 2021/213; G01J 4/00; G01B 11/0641
USPC ........................................................ 356/369
See application file for complete search history.

(56) References Cited

U.S. PATENT DOCUMENTS 5,608,526 A    3/1997   Piwonka-Corle et al.
5,859,424 A    1/1999   Norton et al.
(Continued)

OTHER PUBLICATIONS

Stewart, James E. and Gallaway, William S., "Diffraction Anomalies in Grating Spectrophotometers," Applied Optics, vol. 1, No. 4, pp. 421-430, Jul. 1962.

(Continued)

*Primary Examiner* — Tarifur Chowdhury
*Assistant Examiner* — Md M Rahman
(74) *Attorney, Agent, or Firm* — Spano Law Group; Joseph S. Spano

(57) ABSTRACT

Methods and systems for performing broadband spectroscopic metrology with reduced sensitivity to grating anomalies are presented herein. A reduction in sensitivity to grating anomalies is achieved by selecting a subset of available system parameter values for measurement analysis. The reduction in sensitivity to grating anomalies enables an optimization of any combination of precision, sensitivity, accuracy, system matching, and computational effort. These benefits are particularly evident in optical metrology systems having large ranges of available azimuth angle, angle of incidence, illumination wavelength, and illumination polarization. Predictions of grating anomalies are determined based on a measurement model that accurately represents the interaction between the measurement system and the periodic metrology target under measurement. A subset of available system parameter values is selected to reduce the impact of grating anomalies on measurement results. The selected subset of available system parameters is implemented on a configurable spectroscopic metrology system performing measurements.

20 Claims, 7 Drawing Sheets

(51) Int. Cl.
*G01N 21/21* (2006.01)
*G01N 21/25* (2006.01)

(56) References Cited

U.S. PATENT DOCUMENTS

| | | | |
|---|---|---|---|
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |
| 6,816,570 B2 | 11/2004 | Janik et al. | |
| 6,895,075 B2 | 5/2005 | Yokhin et al. | |
| 6,972,852 B2 | 12/2005 | Opsal et al. | |
| 7,450,225 B1 | 11/2008 | Liu et al. | |
| 7,463,369 B2* | 12/2008 | Wack | G01B 11/24 356/364 |
| 7,478,019 B2 | 1/2009 | Zangooie et al. | |
| 7,602,509 B1 | 10/2009 | Hench | |
| 7,698,098 B2 | 4/2010 | Ritter et al. | |
| 7,826,071 B2 | 11/2010 | Shchegrov et al. | |
| 7,826,072 B1 | 11/2010 | Wack et al. | |
| 7,921,383 B1 | 4/2011 | Wei | |
| 7,929,667 B1 | 4/2011 | Zhuang et al. | |
| 7,933,026 B2 | 4/2011 | Opsal et al. | |
| 8,289,527 B2 | 10/2012 | Li et al. | |
| 8,296,687 B2 | 10/2012 | Strang et al. | |
| 9,217,717 B2* | 12/2015 | Flock | G01N 21/9501 |
| 9,228,943 B2 | 1/2016 | Wang et al. | |
| 2003/0187604 A1 | 10/2003 | Drege et al. | |
| 2007/0229852 A1* | 10/2007 | Wack | G01B 11/24 356/625 |
| 2008/0049214 A1 | 2/2008 | Maznev et al. | |
| 2012/0323356 A1 | 12/2012 | Dziura et al. | |
| 2013/0114085 A1 | 5/2013 | Wang et al. | |
| 2013/0321810 A1* | 12/2013 | Wang | G01N 21/211 356/369 |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2015/0042984 A1 | 2/2015 | Pandev et al. | |
| 2015/0046118 A1 | 2/2015 | Pandev et al. | |

OTHER PUBLICATIONS

Li, Xuanhua, et al., "Dual Plasmonic Nanostructures for High Performance Inverted Organic Solar Cells," Adv. Mater., 24, 3046-3052, 2012.

Chetvertukhin, A.V., et al., "Magneto-optical Kerr Effect Enhancement at the Wood's Anomaly in Magnetoplasmonic Crystals," Journal of Magnetism and Magnetic Materials, 324, 3516-3518, 2012.

Sondergaard, Thomas, et al., "Extraordinary Optical Transmission With Tapered Slits: Effect of Higher Diffraction and Slit Resonance Orders," J. Opt. Soc. Am. B, vol. 29, No. 1, pp. 130-137, Jan. 2012.

Vial, Benjamin, et al., "Adaptive Perfectly Matched Layer for Wood's Anomalies in Diffraction Gratings," Optics Express 28094, vol. 20, No. 27, Dec. 17, 2012.

Hessel, A. and Oliner, A.A., "A New Theory of Wood's Anomalies on Optical Gratings," Applied Optics, vol. 4, No. 10, pp. 1275-1297, Oct. 1965.

* cited by examiner

OPTICAL METROLOGY WITH REDUCED SENSITIVITY TO GRATING ANOMALIES

CROSS REFERENCE TO RELATED APPLICATION

The present application for patent claims priority under 35 U.S.C. §119 from U.S. provisional patent application Ser. No. 62/111,421, entitled "Apparatus and Methods for Arbitrary AOI and AZ angle Measurement of Semiconductor Structure Critical Dimensions," filed Feb. 3, 2015, the subject matter of which is incorporated herein by reference in its entirety.

TECHNICAL FIELD

The described embodiments relate to metrology systems and methods, and more particularly to methods and systems for improved measurement of semiconductor structures.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Ongoing reductions in feature size, increasing geometric complexity, and more diverse material compositions of semiconductor devices impose difficult requirements on optical metrology systems that are relied upon for process development and process monitoring.

Optical metrology systems must meet high precision and accuracy requirements for increasingly small metrology targets at high throughput (i.e., short move, acquire, and measure (MAM) times) to remain cost effective. In this context, measurement model compute times have emerged as a performance limiting issue in the design of optical metrology systems. More specifically, performing measurement model calculations with sufficient accuracy, particularly during high throughput operation (i.e., short MAM times) has become an important issue for optical metrology systems, particularly those systems offering large ranges of system parameter options.

In some examples, spectroscopic scatterometry measurements performed at multiple angles of incidence (AOI) and multiple azimuth angles have emerged in response to current metrology challenges. In some examples, these systems are configured rotating polarizer (RP) configurations and rotating polarizer, rotating compensator (RPRC) ellipsometry configurations. These systems offer ranges of available system parameters. For example, different values of azimuth angle, angle of incidence, illumination wavelength, and illumination polarization may be selected for particular measurements. These ranges of available system parameters are useful for increasing measurement sensitivity to parameters of interest and increasing measurement diversity that is useful for breaking correlations among parameters of interest.

Unfortunately, as metrology targets become more complex, so does the spectral polarization response of the metrology target. For example, the spectroscopic measurement of periodic targets sometimes results in large spectral variations and discontinuities. These measurement effects are sometimes termed grating anomalies, or Wood's anomalies. Some models of these grating anomalies are relatively simple, such as the reflection (or transmission) Rayleigh manifold. However, often these simplified models fail to sufficiently capture the observed grating anomalies present in spectroscopic measurements of current metrology targets. Other resonances triggered by the penetration of the illumination light into the grating structures themselves are visible as grating anomalies in the spectroscopic measurements. These resonances are difficult to incorporate directly into a measurement model. Thusfar, the regression of a measurement model capable of repeatably resolving parameters of interest from spectral data exhibiting grating resonance anomalies is far too computationally expensive for practical use. In some examples, simply excluding the spectral range where an anomaly arises causes regression results to suffer systematical errors. In extreme cases, this results in a failure of the metrology system to monitor the process.

The risk of triggering significant grating anomalies in the collected data increases when the measurement of a parameter of interest involves ranges of system parameter values such as azimuth angle, angle of incidence, illumination wavelength, and illumination polarization. Furthermore, the risks are highly dependent on parameters of the metrology target structure, such as pitch (period) in a 2-D grating and multiple grating pitches in different directions (e.g., orthogonal gratings in a 3-D grating structure).

Future metrology applications present challenges due to small feature size and multi-parameter correlation. Improvements to ellipsometer and reflectometer systems incorporating ranges of system parameter values such as azimuth angle, angle of incidence, illumination wavelength, illumination polarization, illumination Numerical Aperture (NA), and collection NA are desired.

SUMMARY

Methods and systems for performing broadband spectroscopic metrology with reduced sensitivity to grating anomalies are presented herein. A reduction in sensitivity to grating anomalies is achieved by selecting a subset of available system parameter values for measurement analysis. This reduction in sensitivity to grating anomalies enables an optimization of any combination of precision, sensitivity, accuracy, system matching, and computational effort. These benefits are particularly evident in optical metrology systems having large ranges of available azimuth angle, angle of incidence, illumination wavelength, illumination polarization, and collection NA.

In one aspect, predictions of grating anomalies are determined based on a measurement model that accurately represents the interaction between the measurement system and the periodic metrology target under measurement. The model is employed as a tool to generate a measurement recipe that avoids excessive contamination of measurement results with grating anomalies. The measurement recipe includes a subset of available measurement system parameters that enables precise estimates of values of parameters of interest associated with the modeled metrology target with reasonable computational effort.

In a further aspect, the selection of the subset of the available values of illumination wavelength, AOI, Az, illumination polarization, illumination NA, and collection NA involves an optimization based on the measurement model. A cost function of the optimization may include metrics indicative of measurement precision, measurement sensitivity to parameters of interest, measurement accuracy, system matching to a metrology reference, computational effort, or any combination thereof. Similarly, a constraint on the optimization may include bounds on a metric indicative of measurement precision, measurement sensitivity to parameters of interest, measurement accuracy, system matching to a metrology reference, computational effort, or any combination thereof. In this manner, a balance between measurement quality and computational effort can be achieved in the selection of the subset of system parameters.

A configurable scatterometer performs optical critical dimension (OCD) measurements of parameters of interest with reduced sensitivity to grating anomalies. The scatterometer system is configured to perform measurements based on a subset of available system parameters such as angle of incidence (AOI), azimuth angle (Az), illumination polarization state, and illumination wavelength. The subset of available system parameter values is selected based on a model of the measurement of a particular metrology target, including its geometric and material properties. The scatterometer configuration is selected to optimize sensitivity to the parameters of interest, measurement precision, measurement accuracy, system matching, and computational effort.

In another further aspect, measurements are improved by incorporating the optical system model at arbitrary Az angles to correct scatterometer signal errors introduced by the non-ideal polarization response of illumination and collection optics. These effects are significant at Az angles other than 0 and 90 degrees.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for performing broadband spectroscopic metrology with reduced sensitivity to grating anomalies are presented herein. A reduction in sensitivity to grating anomalies is achieved by selecting a subset of available system parameter values for measurement analysis. This reduction in sensitivity to grating anomalies enables an optimization of any combination of precision, sensitivity, accuracy, system matching, and computational effort. These benefits are particularly evident in optical metrology systems having large ranges of available azimuth angle, angle of incidence, illumination wavelength, and illumination polarization.

In one aspect, a configurable scatterometer performs optical critical dimension (OCD) measurements of parameters of interest with reduced sensitivity to grating anomalies. The scatterometer system is configured to perform measurements based on a subset of available system parameters such as angle of incidence (AOI), azimuth angle (Az), illumination polarization state, illumination wavelength, illumination NA, and collection NA. The subset of available system parameter values is selected based on a model of the measurement of a particular metrology target, including its geometric and material properties. The scatterometer configuration is selected to optimize sensitivity to the parameters of interest, measurement precision, measurement accuracy, system matching, and computational effort.

Figure 1:
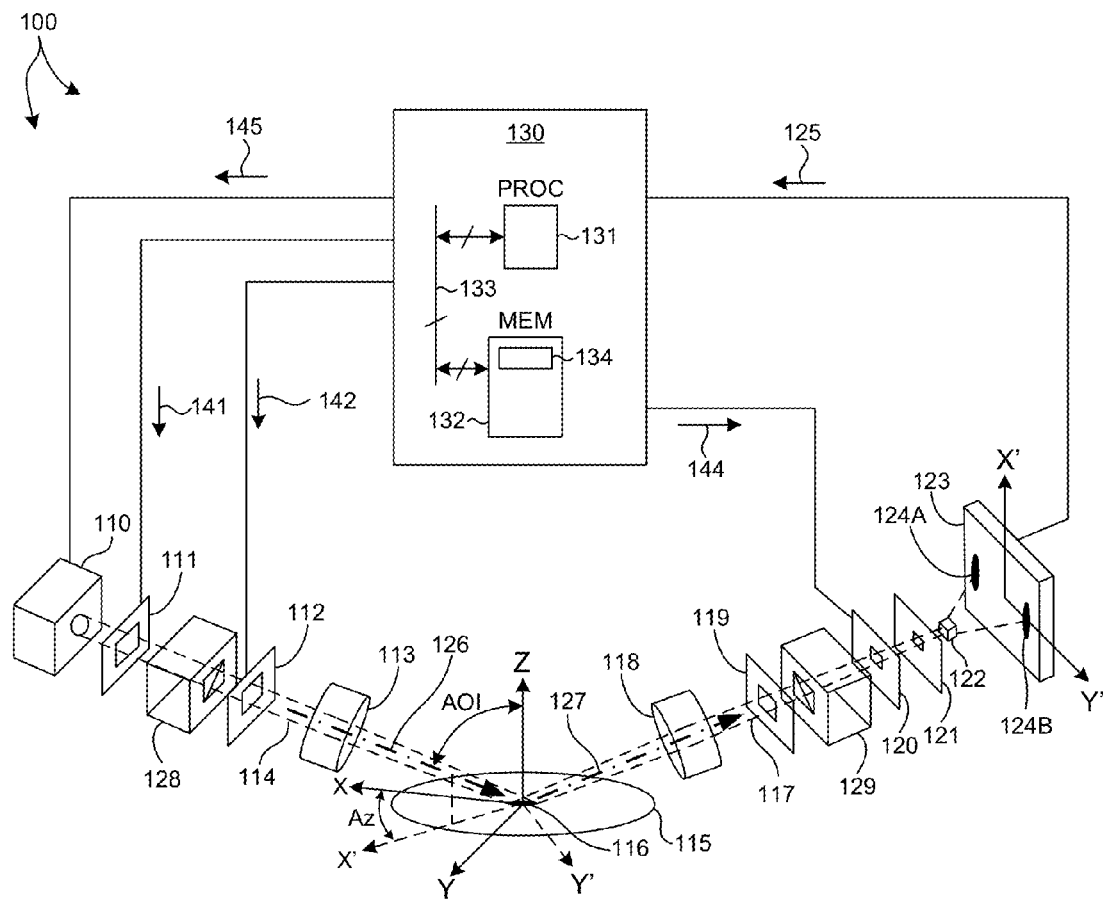
FIG. 1 depicts an exemplary metrology system 100 having reduced sensitivity grating anomalies.

FIG. 1 depicts an exemplary, metrology system 100 having reduced sensitivity to grating anomalies. Metrology system 100 may be configured as a broadband spectroscopic ellipsometer, reflectometer, or any combination thereof. Metrology system 100 includes an illumination source 110 that generates a beam of illumination light 114 incident on a wafer 115. The beam of illumination light 114 passes through illumination pupil 111, polarizer element 128, illumination field stop 112, and illumination optics 113 as the beam propagates from the illumination source 110 to wafer 115. Beam 114 illuminates a portion of wafer 115 over a measurement spot 116. A beam of collected light 117 is collected from measurement spot 116 by collection optics 118. Collected light 117 passes through collection field stop 119, compensator element 129, collection pupil 120, and spectrometer slit 121. The beam of collected light 117 is diffracted by diffraction grating 122 to spatially disperse the beam of collected light according to wavelength. The wavelength dispersed, collected light is incident on the surface of a two dimensional detector. In one example, detector 123 is a charge coupled device (CCD). However, in general, other two dimensional detector technologies may be contemplated (e.g., a position sensitive detector (PSD), an infrared detector, a photovoltaic detector, etc.). Detector 123 converts the collected light into electrical signals 125 indicative of spectral intensity of the collected light. As depicted in FIG. 1, the collected beam of light 117 includes two distinct wavelengths, by way of non-limiting example. Diffraction grating 122 causes a spatial separation between the two different wavelengths of light projected onto the surface of detector 123. In this manner, light collected from measurement spot 116 having a particular wavelength is projected onto detector 123 over spot 124A and light collected from measurement spot 116 having another, different wavelength is projected onto detector 123 over spot 124B.

As depicted in FIG. 1, the beam of illumination light 114 is provided to the surface of wafer 115 at an oblique angle. In general, illumination light may be provided to the surface of wafer 115 at any oblique angle or number of oblique angles. In some embodiments, an amount of illumination light is provided to the surface at normal incidence (i.e., aligned with the surface normal) in addition to oblique illumination.

In a further aspect, the amount of illumination light is broadband illumination light that includes a range of wavelengths spanning at least 500 nanometers. In one example, the broadband illumination light includes wavelengths below 250 nanometers and wavelengths above 750 nanometers. In general, the broadband illumination light includes wavelengths between 150 nanometers and 2,500 nanometers. In some embodiments the broadband illumination light includes wavelengths between 190 nanometers and 860 nanometers. In some examples, the emission spectrum of the broadband light source includes one or more characteristic atomic lines, e.g., from a Xenon arc lamp light source. In some embodiments, the broadband light source is a high brightness Laser Driven Light Source (LDLS). In general, any suitable illumination source may be contemplated within the scope of this patent document, including one or more narrowband light sources.

As depicted in FIG. 1, the Z-axis is oriented normal to the surface of wafer 115. The X and Y axes are coplanar with the surface of wafer 115, and thus perpendicular to the Z-axis. The chief ray 126 of the beam of illumination light 114 and the chief ray 127 of the beam of collected light 117 define a plane of incidence that is perpendicular to the XY plane. The beam of illumination light 114 is incident on the surface of wafer 115 at an angle of incidence, AOI, with respect to the Z-axis and lies within the plane of incidence, X'Z. The plane of incidence is oriented with respect to a coordinate frame, XY, fixed to wafer 116 at an azimuth angle, Az.

Figure 4A:
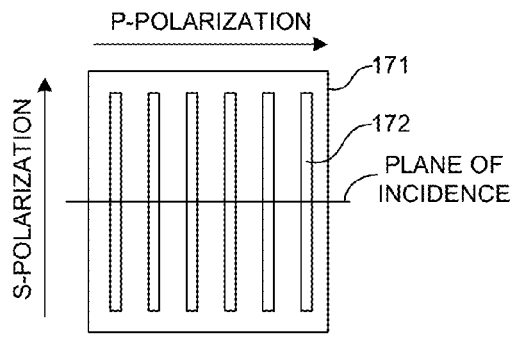
FIG. 4A depicts a top-view of a two-dimensional grating structure 172 disposed on a substrate 171. In this illustration, the plane of incidence is aligned perpendicular to the direction of the grating lines of grating structure 172, or parallel to the grating vector as defined along the grating pitch direction.
Figure 5A:
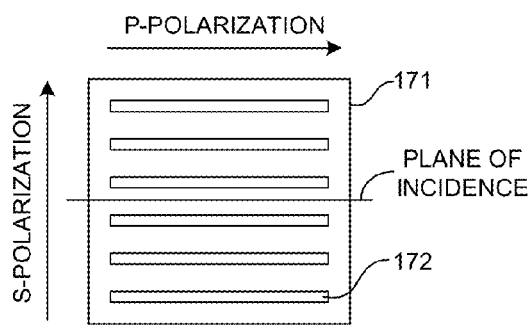
FIG. 5A depicts a top-view of a two-dimensional grating structure 172 disposed on a substrate 171. In this illustration, the plane of incidence is aligned parallel to the direction of the grating lines of grating structure 172.

In some examples, the azimuth angle is defined such that the zero azimuth angle is aligned across a grating structure of wafer 116. For example, FIG. 4A depicts a top-view of two-dimensional grating structure 172 disposed on a substrate 171. In this illustration, the plane of incidence is aligned perpendicular to the direction of the grating lines of grating structure 172. This orientation of the angle of incidence with respect to the grating structure is often defined as the zero azimuth angle. Similarly, FIG. 5A illustrates a top view of the two-dimensional grating structure 172 disposed on the substrate 171. In this illustration, the plane of incidence is aligned parallel with the grating lines of grating structure 172. This orientation of the angle of incidence with respect to the grating structure is often defined as the ninety degree azimuth angle.

The geometric projection of a beam of illumination light onto the surface of a specimen at an oblique angle results in an elongation of the illumination beam cross-section in the direction aligned with the plane of incidence. By way of non-limiting example, a circular beam of illumination light projected on the wafer surface results in an illumination area that is elliptical in shape. Thus, in general, oblique illumination of a surface results in a projected illumination area that is elongated relative to the illumination cross section and the direction of elongation is aligned with the plane of incidence. Moreover, the magnitude of the elongation increases as the angle of incidence increases. More specifically, the beam shape is inversely proportional to the cosine of the angle of incidence in the direction of the plane of incidence. In the absence of diffraction and aberration effects, the projected illumination light remains undistorted in the direction perpendicular to the plane of illumination (e.g., Y'-direction).

As depicted in FIG. 1, measurement spot 116 is projected onto the surface of detector 123 in a wavelength dispersive manner. Metrology system 100 is configured such that the projection of the elongated direction of measurement spot 116 is oriented perpendicular to the direction of wavelength dispersion on the surface of detector 123. The X'-axis depicted in FIG. 1 is representative of the projection of the elongated direction of measurement spot 116 (i.e., the X'-axis) onto detector 123. As depicted in FIG. 1, the projection of the X'-axis onto detector 123 is oriented perpendicular to the direction of wavelength dispersion on the surface of detector 123. In some other embodiments, the elongated direction of the measurement spot is oriented parallel to the direction of wavelength dispersion on the surface of detector 123.

Figure 2:
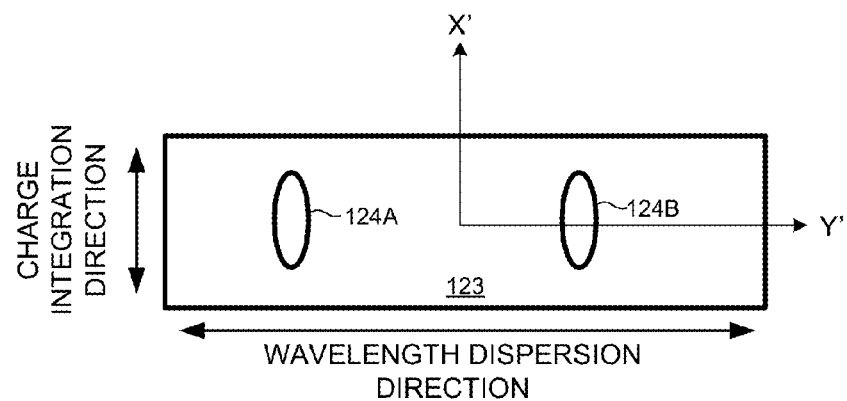
FIG. 2 depicts a normal view of the surface of detector 123 depicted in FIG. 1, including images 124A and 124B of measurement spot 116 projected onto detector 123.

FIG. 2 depicts a normal view of the surface of detector 123. As depicted in FIG. 2, the projection of the elongated direction of measurement spot 116 (i.e., X'-axis) is oriented perpendicular to the direction of wavelength dispersion across the surface of detector 123. By way of example, the elongated direction of spots 124A and 124B is oriented perpendicular to the wavelength dispersion direction. The wavelength dependent images (e.g., spots 124A and 124B) on the surface of detector 123 are integrated in the direction perpendicular to the wavelength dispersion direction to obtain a spectrum, i.e., intensity as a function of wavelength along the wavelength dispersion axis. For a CCD detector, charge is integrated in the direction perpendicular to wavelength dispersion to arrive at the spectrum.

In the embodiment depicted in FIG. 1, the images projected onto the surface of the detector (e.g., CCD 123) are integrated in the direction perpendicular to the spectrometer wavelength dispersive axis at each wavelength to obtain the measured spectrum. The individual spectral shape at each wavelength is the point spread function (PSF) of the system at that specific wavelength.

Figure 3:
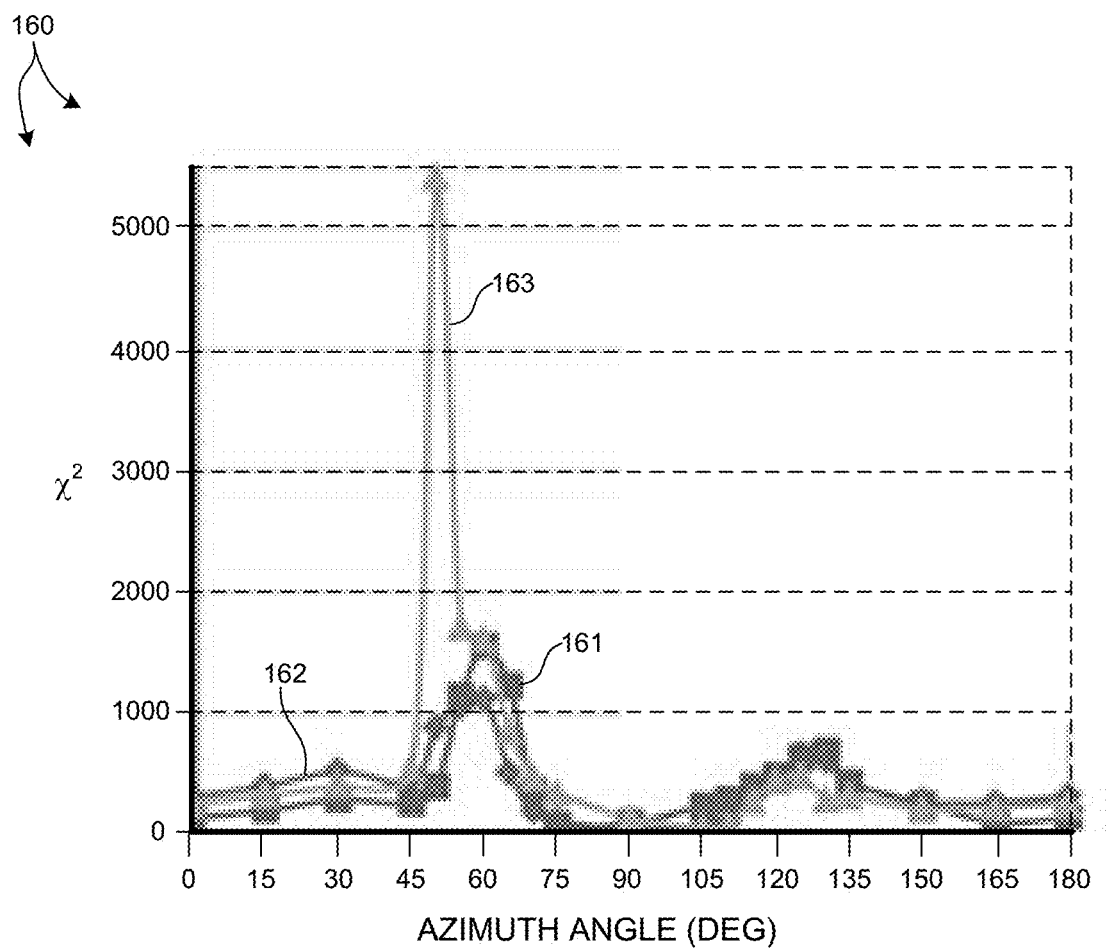
FIG. 3 depicts a plot 160 indicating the goodness of fit associated with a critical dimension measurement of a known grating target by a metrology system such as metrology system 100.

FIG. 3 depicts a plot 160 indicating the goodness of fit (expressed as chi-squared values) associated with a critical dimension measurement of a known grating target by a metrology system such as metrology system 100. The measurements are performed over a range of azimuth angles and three different angles of incidence illustrated by plotlines 161, 162, and 163. If the physical measurement system and the associated measurement model both perform well, deviations of measured results from modeled results should be small and one would expect to see small chi-squared values across the range of available azimuth angles and angles of incidence. However, as depicted in FIG. 3, there are pronounced peaks associated with the chi-squared values for all three angles of incidence in the range of azimuth angles from approximately 45 degrees to 75 degrees. In addition, another, weaker feature is also observed at an azimuth angle of approximately 135 degrees. As depicted in FIG. 3, the presence and magnitude of the induced errors depends both on angle of incidence and azimuth angle. These measurement errors are induced by the interaction of the grating structure with broadband illumination. In some examples, the grating anomalies visible in the measured spectra are due to resonance phenomena induced in the grating target. These observed phenomena are sometimes referred to as Wood's anomalies. Grating anomalies depend on the specific structure being probed by the illumination light. Features such as CD pitch, linewidth, structure depth, and material dispersion strongly affect the nature of the observed grating anomalies. In addition, the observed grating anomalies are also strongly dependent on the polarization states of the illumination light.

In one aspect, predictions of grating anomalies are determined based on a measurement model that accurately represents the interaction between the measurement system and the periodic metrology target under measurement. The model is employed as a tool to generate a measurement recipe that avoids excessive contamination of measurement results with grating anomalies. The measurement recipe includes a subset of available measurement system parameters that enables precise estimates of values of parameters of interest associated with the modeled metrology target with reasonable computational effort.

Figure 6:
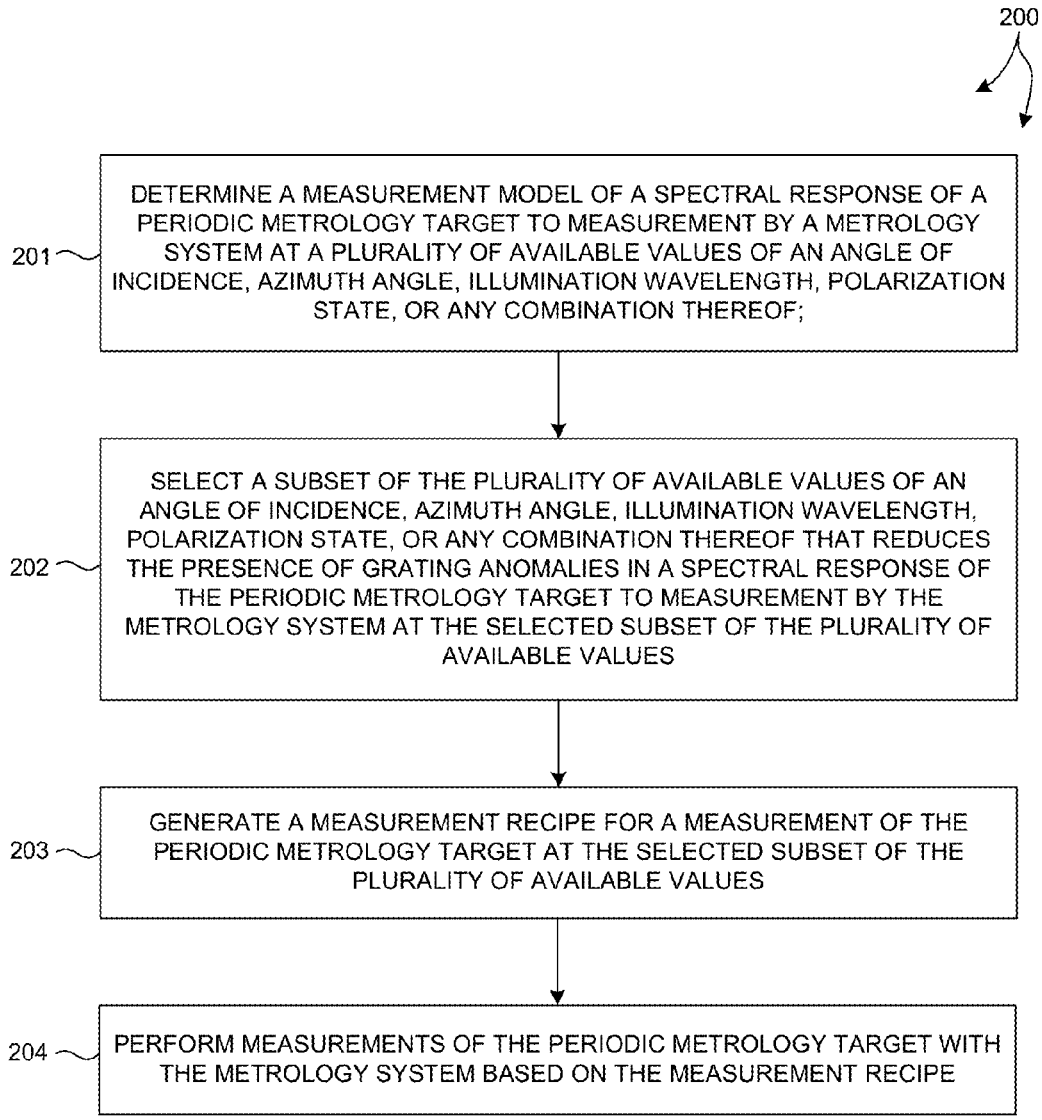
FIG. 6 illustrates a flowchart of a method 200 of performing spectroscopic measurements in at least one novel aspect as described herein.

FIG. 6 illustrates a method 200 of performing spectroscopic measurements in at least one novel aspect. Method 200 is suitable for implementation by a metrology system such as metrology system 100 illustrated in FIG. 1 of the present invention. In one aspect, it is recognized that data processing blocks of method 200 may be carried out via a pre-programmed algorithm executed by one or more processors of computing system 130, or any other general purpose computing system. It is recognized herein that the particular structural aspects of metrology system 100 do not represent limitations and should be interpreted as illustrative only.

In block 201, a measurement model of a spectral response of a periodic metrology target to measurement by a metrology system is determined at a plurality of available values of an angle of incidence, azimuth angle, illumination wavelength, polarization state, or any combination thereof.

As illustrated in FIG. 3, grating anomalies result in measurement errors under normal measurement system operation. In some examples, the real-time measurement model or pre-computed measurement library is unable to converge to a solution in the presence of grating anomalies. In some examples, the use of a higher truncation order may enable the measurement model or pre-computed measurement library to converge to a solution within acceptable error levels, but very often the computational burden associated with this approach is impractical, and thus not feasible for implementation as part of a metrology tool for semiconductor processing.

To address this problem, a measurement model sensitive to grating anomalies for the specific metrology target under consideration and the specific metrology system configuration is determined.

In some examples, a model of the reflection (or transmission) Rayleigh manifold is employed to identify one or more grating anomalies. Rayleigh manifolds are defined as those combinations of wavelength, angle of incidence, and azimuth angle when the component of the propagation of the illumination light in the vertical direction is zero This condition triggers either evanescent waves or propagating waves inside the grating structure. Both phenomena could be the precursor of a Wood's anomaly.

For a 2-D grating having a fixed pitch, the in-air Rayleigh wavelengths are defined by equation (1), where $\lambda_R$, is the Rayleigh wavelength, p, is the pitch of the grating structure, m, is the diffraction order, $\theta$, is the angle of incidence, and $N_I$, is the index of refraction of the region above the grating (e.g., air, a bulk layer, etc.).

$$\lambda_R = \frac{N_I p}{m}(\sin\theta \pm 1) \qquad (1)$$

For a 3-D grating having a fixed pitch in two orthogonal directions, the Rayleigh wavelengths are defined by equation (2), where $\lambda_R$, is the Rayleigh wavelength, $\Lambda x$ and $\Lambda y$ is the grating pitch in x and y direction, respectively, m and n is the diffraction order in the x and y direction, respectively, $\theta$, is the angle of incidence, $\varphi$, is the azimuth angle, and $N_I$, is the index of refraction of the region above the grating (e.g., air, a bulk layer, etc.)

$$\lambda_R = \frac{\sin\theta\left(\frac{m}{\Lambda_x}\cos\varphi + \frac{n}{\Lambda_y}\sin\varphi\right) \pm \sqrt{\sin^2\theta\left(\frac{m}{\Lambda_x}\cos\varphi + \frac{n}{\Lambda_y}\sin\varphi\right)^2 + \cos^2\theta\left(\frac{m^2}{\Lambda_x^2} + \frac{n^2}{\Lambda_y^2}\right)}}{\frac{m^2}{\Lambda_x^2} + \frac{n^2}{\Lambda_y^2}} \qquad (2)$$

In some examples, a model of the Rayleigh manifold within the grating is employed to identify one or more grating anomalies. Calculation of grating Rayleigh manifolds is described in detail in U.S. Pat. No. 7,602,509, issued on Oct. 13, 2009, assigned to KLA-Tencor Technologies Corp., the content of which is incorporated herein by reference in its entirety. In one example, the angle of incidence associated with the Rayleigh condition, $\theta_R$, is estimated by equation (3), where $\lambda$, is the illumination wavelength, p, is the pitch of the grating structure, m, is the diffraction order, and $N_S$, is the mean index of refraction of the grating region.

$$\theta_R = \sin^{-1}\left(\frac{1}{N_I}\left(m\frac{\lambda}{p} \pm N_S\right)\right) \qquad (3)$$

For example, if the grating region contains two materials with index of refraction $N_A$ and $N_B$ and their relative widths are ½ of the pitch, then the effective media approximation will give a mean index of refraction as illustrated in equation (4).

$$N_S = \frac{1}{2}N_A + \frac{1}{2}N_B \quad (4)$$

The existence of a Rayleigh wavelength in the spectral range of interest potentially introduces numerical aperture (NA) averaging inaccuracy. This leads to poor agreement between measured data and regression results.

Figure 4B:
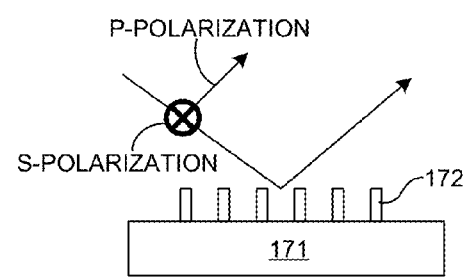
FIG. 4B depicts a side-view of the two-dimensional grating structure 172 disposed on substrate 171 depicted in FIG. 4A.

In another example, a model of the S and P anomalies as a function of illumination polarization is employed to identify one or more grating anomalies. FIGS. 4A-B and FIGS. 5A-B illustrate the relationship between the P-anomaly and the S-anomaly with a 2-D grating target for two special case orientations of the 2-D grating target with respect to the plane of incidence. FIG. 4A illustrates a top view of a periodic grating target 172 disposed on a substrate 172 for the instance when the plane of incidence (e.g., plane X'Z illustrated in FIG. 1) is parallel to the pitch direction and perpendicular to the grating lines. As illustrated in FIG. 4A, the P-polarization of the illumination light is parallel to the plane of incidence and the S-Polarization of the illumination light is perpendicular to the plane of incidence. FIG. 4B illustrates a side view of the instance depicted in FIG. 4A. A described hereinbefore, this orientation of the plane of incidence with respect to the grating pitch is typically defined as the zero azimuth angle.

The orientation of the 2-D grating target with respect to the plane of incidence depicted in FIGS. 4A-4B may give rise to an S-anomaly with strong S-polarization, and under the condition that the grating structure and material induced resonance criteria are met. Illumination light s-polarization state parallel to grating lines and perpendicular to pitch is the prerequisite for S-anomaly. Hence, the S-anomaly may occur at the zero azimuth angle.

Figure 5B:
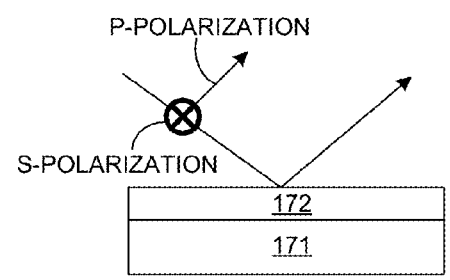
FIG. 5B depicts a side-view of the two-dimensional grating structure 172 disposed on substrate 171 depicted in FIG. 5A.

FIG. 5A illustrates a top view of the periodic grating target 172 disposed on the substrate 172 for the instance when the plane of incidence (e.g., plane X'Z illustrated in FIG. 1) is perpendicular to the pitch direction and parallel to the grating lines. As illustrated in FIG. 5A, the P-polarization of the illumination light is parallel to the plane of incidence and the S-Polarization of the illumination light is perpendicular to the plane of incidence. FIG. 5B illustrates a side view of the instance depicted in FIG. 5A. This orientation of the plane of incidence with respect to the grating pitch is typically associated with an azimuth angle of ninety degrees.

The orientation of the 2-D grating target with respect to the plane of incidence depicted in FIGS. 5A-5B may give rise to a P-anomaly with strong P-polarization, and under the condition that the grating structure and material induced resonance criteria are met. Illumination light p-polarization state parallel to grating lines and perpendicular to pitch is the prerequisite for P-anomaly. Hence, the P-anomaly may occur at the ninety degree azimuth angle.

In general, the grating anomalies associated with the S-anomaly and the P-anomaly are coupled to grating orientation with respect to plane of incidence (i.e., azimuth angle). When the azimuth angle is an angle other than zero degrees or ninety degrees, the coupling of the P-anomaly and the S-anomaly becomes more complex.

In some examples, a rigorous couple wave analysis (RCWA) model or a finite electromagnetic model (FEM) of the measurement of a periodic metrology target is employed. Although these models are provided by way of example, other suitable models may be contemplated within the scope of this patent document. The measurement model predicts the spectral response of the periodic metrology target to measurement by the metrology system, and any associated grating anomalies.

In one example, an RCWA or FEM model is employed to correctly represent the resonance phenomena. These models are specific to the metrology system configuration and metrology target structure. For example, these models capture the effect of propagating and evanescent waves inside the grating structure, as well as resonance (e.g., Wood's anomaly), and the location of a Wood's anomaly within the collection NA for all available wavelengths, angles of incidence, azimuth angle, and illumination polarization. In many examples, 3-D metrology targets are stacked, multi-layer structures. For complex, 3-D metrology targets, grating anomalies triggered in one layer tend to couple into adjoining layers, leading to unexpected spectral measurement results. For practical measurement purposes, once grating anomalies are triggered within a complex, 3-D structure, accurate measurement results become computationally expensive, if not impossible.

As described herein, first principles models such as RCWA or FEM models are utilized to predict the onset of resonant phenomena within a complex, 3-D structure, and identify the subset of system parameter values that give rise to grating anomalies in the structure. Furthermore, as described herein, the metrology system is configured to effectively exclude the subset of system parameter values that give rise to grating anomalies in the structure. By avoiding the onset of resonant phenomena within a complex, 3-D structure, accurate measurement results are obtained from a relative simple (computationally inexpensive) measurement model.

In a further aspect, the computational burden associated with the measurement model is characterized by a truncation order associated with an iterative regression of the measurement model. With higher truncation order, a first principles model such as an RCWA model is able to properly account for grating anomalies and arrive at precise estimates of values of parameters of interest (e.g., CD, SWA, Height, etc.). With smaller truncation order, errors in parameter estimation result due to inadequate characterization of grating anomalies.

Figure 7:
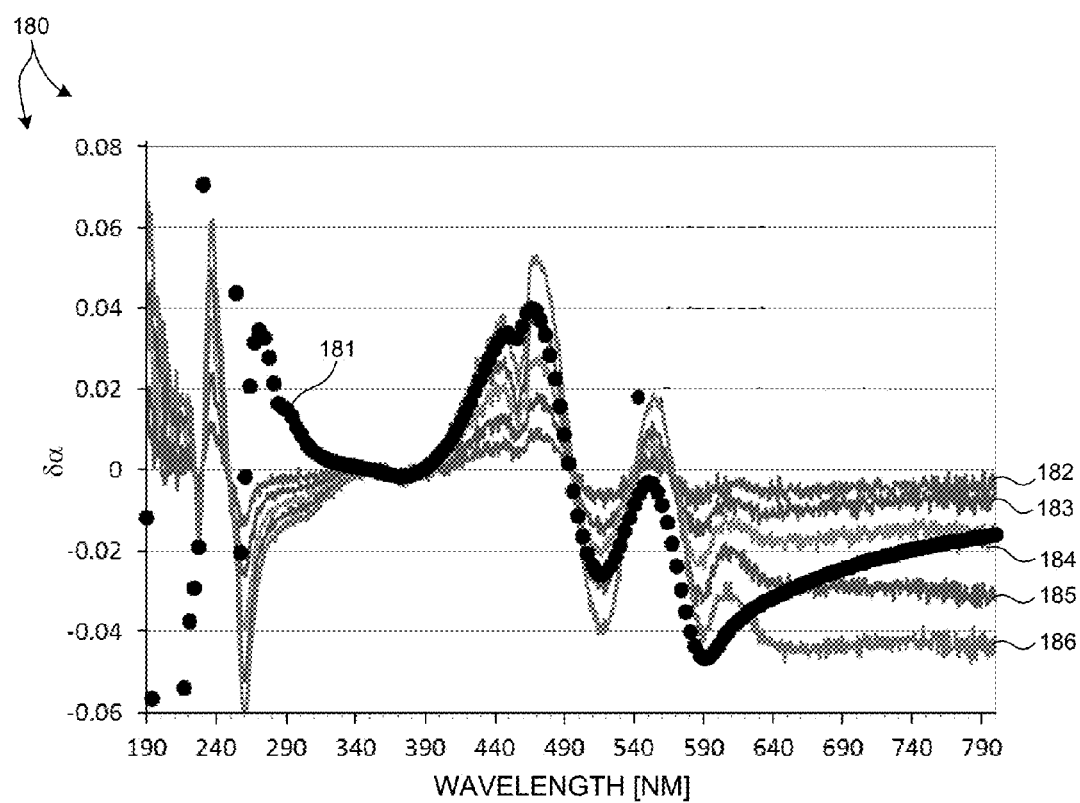
FIG. 7 depicts a plot 180 including a plotline 181 indicative of the difference in spectral parameter, $\alpha$, predicted by a multivariable RCWA measurement model with different truncation orders. In addition, FIG. 7 also includes plotlines 182-186 indicative of the difference in spectral parameter, $\alpha$, measured with a fixed illumination spot size for different sized metrology targets.

FIG. 7 depicts a plot 180 including a plotline 181 indicative of the difference in spectral parameter, $\alpha$, predicted by a multivariable RCWA measurement model with a truncation order of 100 and a truncation order of 5. As illustrated by plotline 181, the differences in the predicted spectra for the two truncation orders are significant, particularly near wavelength ranges exhibiting grating wavelength anomalies.

Figure 8:
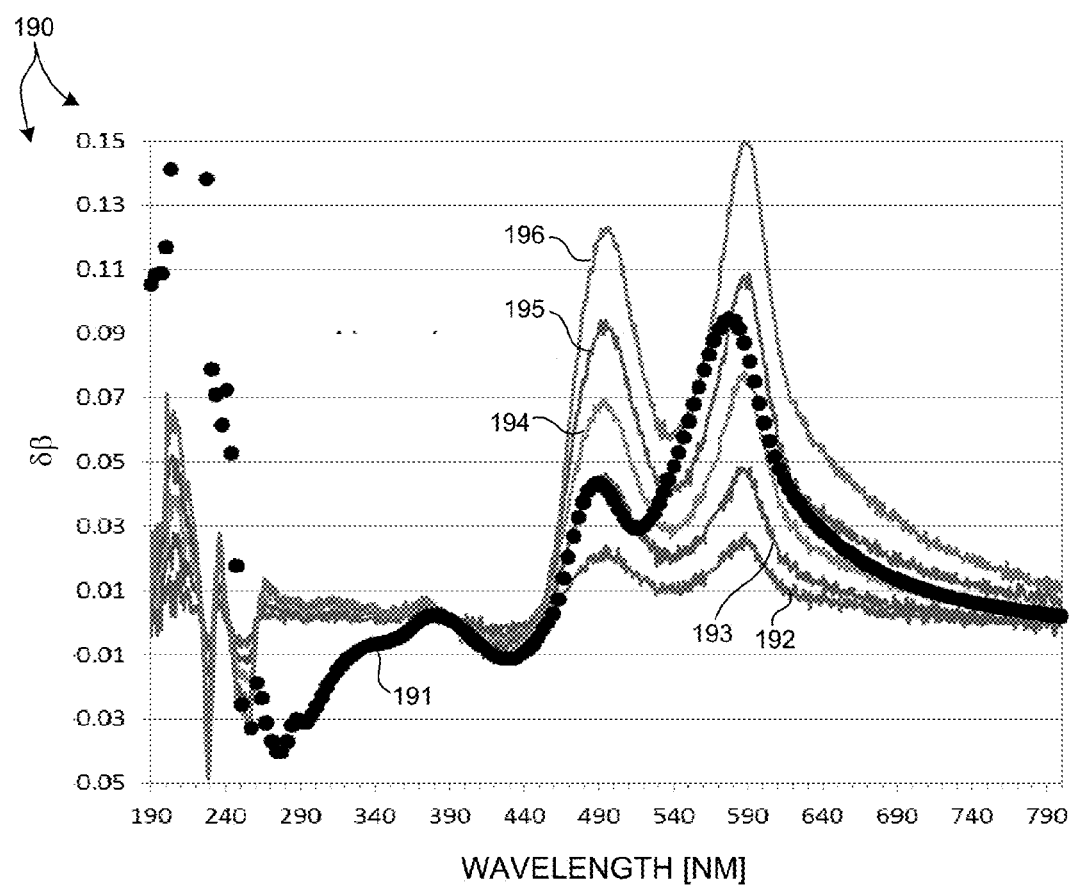
FIG. 8 depicts a plot 190 including a plotline 191 indicative of the difference in spectral parameter, $\beta$, predicted by a multivariable RCWA measurement model with different truncation orders. In addition, FIG. 8 also includes plotlines 192-196 indicative of the difference in spectral parameter, $\beta$, measured with a fixed illumination spot size for different sized metrology targets.

Similarly, FIG. 8 depicts a plot 190 including a plotline 191 indicative of the difference in spectral parameter, $\beta$, predicted by a multivariable RCWA measurement model with a truncation order of 100 and a truncation order of 5. As illustrated by plotline 191, the differences in the predicted spectra for the two truncation orders are significant, particularly near wavelength ranges exhibiting grating wavelength anomalies.

In some examples, the beam size of the amount of illumination light 114 projected onto the surface of wafer 115 is smaller than a size of a measurement target that is measured on the surface of the specimen. Exemplary beam shaping techniques are described in detail in U.S. Pat. No. 9,228,943 issued on Jan. 5, 2016, assigned to KLA-Tencor Corporation, the contents of which are incorporated herein by reference in their entirety.

In a further aspect, the measurement model includes an optical model of the measurement system that characterizes the illumination spot size relative to the size of the metrology target. As the size of the metrology target shrinks closer to the size of the illumination spot, boundary effects begin to impact the interaction of the illumination light with the grating structure. This has a tendency to amplify the presence of grating anomalies.

FIG. 7 depicts a plot 180 that also includes plotlines 182-186 indicative of the difference in spectral parameter, $\alpha$, measured with a fixed illumination spot size (e.g., known point spread function with size compatible to measurement target size) for different sized metrology targets. Plotline 182 illustrates the difference in the spectral parameter, $\alpha$, associated with measurements of a 100 micrometer target and measurements of a 50 micrometer target. Plotline 183 illustrates the difference in the spectral parameter, $\alpha$, associated with measurements of a 100 micrometer target and measurements of a 40 micrometer target. Plotline 184 illustrates the difference in the spectral parameter, $\alpha$, associated with measurements of a 100 micrometer target and measurements of a 30 micrometer target. Plotline 185 illustrates the difference in the spectral parameter, $\alpha$, associated with measurements of a 100 micrometer target and measurements of a 25 micrometer target. Plotline 186 illustrates the difference in the spectral parameter, $\alpha$, associated with measurements of a 100 micrometer target and measurements of a 20 micrometer target.

Similarly, FIG. 8 depicts a plot 190 that also includes plotlines 192-196 indicative of the difference in spectral parameter, $\beta$, measured with a fixed illumination spot size (e.g., known point spread function with size compatible to measurement target size) for different sized metrology targets. Plotline 192 illustrates the difference in the spectral parameter, $\beta$, associated with measurements of a 100 micrometer target and measurements of a 50 micrometer target. Plotline 193 illustrates the difference in the spectral parameter, $\beta$, associated with measurements of a 100 micrometer target and measurements of a 40 micrometer target. Plotline 194 illustrates the difference in the spectral parameter, $\beta$, associated with measurements of a 100 micrometer target and measurements of a 30 micrometer target. Plotline 195 illustrates the difference in the spectral parameter, $\beta$, associated with measurements of a 100 micrometer target and measurements of a 25 micrometer target. Plotline 196 illustrates the difference in the spectral parameter, $\beta$, associated with measurements of a 100 micrometer target and measurements of a 20 micrometer target.

As illustrated by plotlines 182-186 and plotlines 192-196, as the metrology target size begins to approach the size of the point spread function, the differences in the measured spectra become significant. The differences are most pronounced near wavelength ranges exhibiting grating wavelength anomalies, indicating the influence of boundary effects.

In block 202, a subset of the plurality of available values of an angle of incidence, azimuth angle, illumination wavelength, polarization state, or any combination thereof is selected to reduce the presence of grating anomalies in a spectral response of the periodic metrology target to measurement by the metrology system at the selected subset of available values.

In one example, a range of wavelengths around the Rayleigh wavelengths is excluded from measurement analysis based on the Rayleigh manifold models described hereinbefore.

In another example, particular ranges of $\lambda$, AOI and Az are excluded from measurement analysis. For example, the Rayleigh manifold models described hereinbefore describe the onset of wave propagation, and potential resonance phenomena as a manifold in $\{AOI, \lambda\}$ space for the 2-D example, and as a manifold in $\{AOI, Az, \lambda\}$ space for the 3-D example. Thus, in general, ranges of system parameter values around any point on the manifold may be subject to exclusion from measurement analysis.

In yet another example, particular ranges of illumination polarization may be excluded from measurement analysis. In one example, S and P anomalies are reduced by excluding particular ranges of illumination polarization as a function of azimuth angle in accordance with the simple model described with reference to FIGS. 4-5, or alternatively with respect to a RCWA or FEM model describing the phenomena.

In a further aspect, the illumination spot size is selected to reduce the presence of grating anomalies in a spectral response of the periodic metrology target to measurement by the metrology system at the selected subset of available values of angle of incidence, azimuth angle, illumination wavelength, polarization state, or any combination thereof.

In a further aspect, the selection of the subset of the available values of illumination wavelength, AOI, Az, and illumination polarization involves an optimization based on the measurement model. A cost function of the optimization may include metrics indicative of measurement precision, measurement sensitivity to parameters of interest, measurement accuracy, system matching to a metrology reference, computational effort, or any combination thereof. Similarly, a constraint on the optimization may include bounds on a metric indicative of measurement precision, measurement sensitivity to parameters of interest, measurement accuracy, system matching to a metrology reference, computational effort, or any combination thereof. In this manner, a balance between measurement quality and computational effort can be achieved in the selection of the subset of system parameters.

Although, a heuristic approach to selection of the subset of system parameter values, this can lead to sub-optimal results. For example, it may be established that a grating anomaly appears for a particular azimuth angle at a particular wavelength and polarization state, and located at specific position in the collection NA. In one approach, the azimuth angle may be excluded, and another azimuth angle selected where this effect does not occur. Another approach might be to exclude the wavelength where the anomaly appears. However, either of these approaches may compromise the measurement precision and accuracy. In one example, if a particular azimuth angle is excluded for all wavelengths and polarization states, an opportunity to measure a parameter of interest at that azimuth angle (e.g., at different wavelengths) with high sensitivity may be missed. In another example, excluding broad ranges of wavelengths may compromise the precision and accuracy of measurement results, and even render regression results unstable.

In block 203, a measurement recipe is generated for the measurement of the periodic metrology target at the selected subset of the plurality of available values. In one aspect, the measurement recipe includes configuring the specific metrology system in accordance with the selected subset of available values of angle of incidence, azimuth angle, illumination wavelength, polarization state, or any combination thereof. In a further aspect, the measurement recipe includes configuring the measurement model including parameterization and selection of truncation order. In another further aspect, the measurement recipe includes library generation.

In one example, the measurement system is configured such that a range of wavelengths around the Rayleigh wavelengths is excluded from measurement analysis. In some embodiments, this is achieved by filtering out the undesired illumination wavelength ranges. In some embodiments the light source is controlled to exclude these wavelengths from emission. For example, as depicted in FIG. 1, computing system 130 communicates a command signal 145 indicative of a desired selection of wavelength ranges to a tunable illumination source 110. In response, tunable illumination source 110 emits light with the desired selection of wavelengths. In some embodiments, the data associated with these wavelengths is excluded from model regression. For example, computing system 130 receives signals 125 indicative of the spectral response detected by CCD 123. In some embodiments, computing system 130 includes a portion of signals 125 associated with the selected wavelength ranges and excludes the portion of signals 125 that are outside these ranges for purposes of regression analysis.

In another example, the illumination polarization is limited to a selected subset of the available illumination polarizations.

In some embodiments, metrology system 100 is configured as a discrete polarizer and rotating compensator system. In these embodiments, measurements are performed at discrete polarizer angles with a continuously rotating compensator (e.g., compensator 129 depicted in FIG. 1) for multiple azimuth angles and angles of incidence. In some embodiments, polarizer 128 includes a rotatable polarizing element and computing system 130 communicates a command signal 141 indicative of a desired polarization state to polarizer 128. In response, polarizer 128 rotates and stops at the desired polarization state. In this manner, metrology system 100 is configured to stop at a fixed polarization angle to discriminate polarization dependent grating anomaly and insert the rotating compensator to eliminate the grating anomaly. In a further aspect, metrology system 100 also includes a selective analyzer angle (not shown). Similarly, computing system 130 communicates a command signal indicative of a desired analyzer angle to the selective analyzer to suppress polarization sensitive resonances when performing arbitrary azimuth angle measurements on a periodic structure.

In some embodiments, metrology system 100 is configured as a rotating polarizer system. In these embodiments, measurements are performed while the polarization state is continuously changing for multiple azimuth angles and angles of incidence.

In some embodiments, metrology system 100 is configured as a rotating polarizer and rotating compensator system. In these embodiments, measurements are performed with a continuously rotating polarizer (e.g., polarizer 128 depicted in FIG. 1) and a continuously rotating compensator (e.g., compensator 129 depicted in FIG. 1) for multiple azimuth angles and angles of incidence.

Regardless of polarization state, in some embodiments, metrology system 100 is also configured to select ranges of AOI and Az for measurement.

In some embodiments, the optics angle is selected to achieve the desired range of AOI. In some embodiments the illumination numerical aperture (NA) is adjusted to achieve the desired range of AOI. As depicted in FIG. 1, computing system 130 communicates a command signal 141 indicative of a desired illumination NA to illumination pupil 111. In response, illumination pupil 111 adjusts the illumination NA to achieve the desired range of AOI. Illumination pupil 111 includes active elements such as moveable slits, knife edges, MEMS based mirror elements, etc., that are configured to adjust the illumination NA.

In some embodiments, the azimuth angle is selected by rotating the metrology target with respect to the plane of incidence of the metrology system. For example, metrology system 100 may include a rotary stage supporting specimen 115. In these embodiments, computing system 130 communicates a command signal to the rotary stage to rotate specimen 115 with respect to the optics system (e.g., rotation about the z-axis depicted in FIG. 1) to achieve the desired azimuth angle.

In some embodiments, metrology system 100 is configured to select ranges of AOI and Az by adjusting the collection NA. As depicted in FIG. 1, computing system 130 communicates a command signal 144 indicative of a desired collection NA to collection pupil 120. In response, collection pupil 120 adjusts the collection NA to achieve the desired ranges of AOI and Az. Collection pupil 120 includes active elements such as moveable slits, knife edges, MEMS based mirror elements, etc., that are configured to adjust the collection NA.

In a further aspect, the dimension of the collection NA is adjusted to increase measurement sensitivity to grating structure specific features, such as undercut or side wall angle, by limiting the range of AOI and azimuthal angles. By limiting the range of AOI and azimuth angles, light rays that are most sensitive to changes in the parameter of interest are detected, while other light rays are absorbed, or otherwise redirected away from the detector. In this manner the detected spectral results that are most sensitive to the structural features of interest are detected, effectively increasing the NA resolution. If all of the light rays are allowed to pass through to the detector, the risk is that the unique spectral features that are most sensitive to structural features of interests are averaged away with the rest of the detected light, effectively smearing the spectral results.

Figure 9:
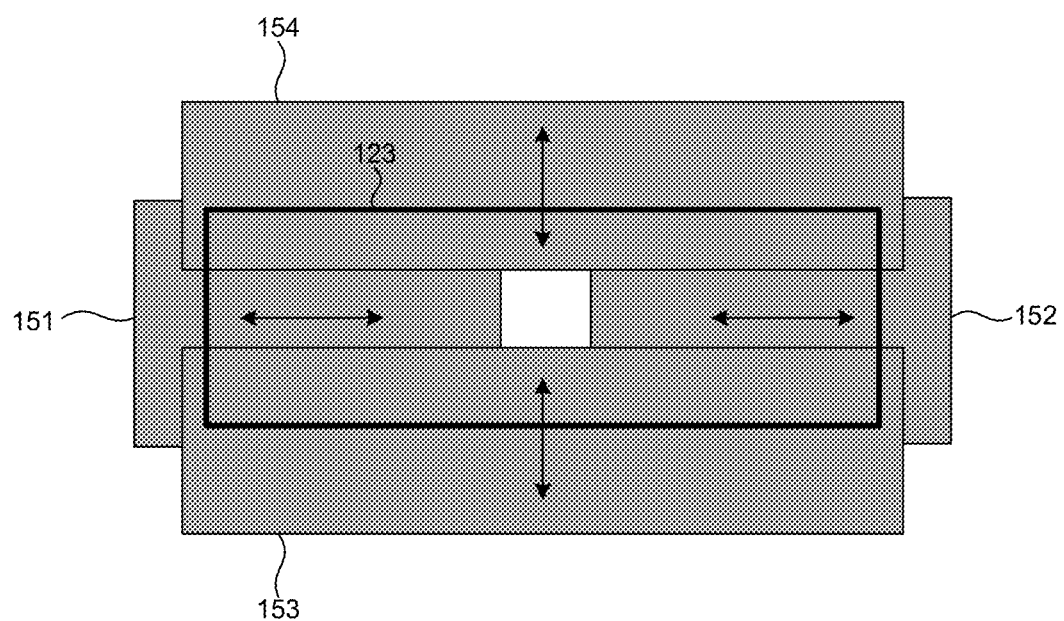
FIG. 9 depicts a configurable collection NA including four moveable absorptive panels 151-154.

In some examples, the size and location of the collection pupil is adjusted. FIG. 9 depicts a configurable collection NA including four moveable absorptive panels 151-154. Depending on the position of the panels, the size and location of the collection pupil is adjusted. In this manner, the ranges of AOI and Az that pass through the collection pupil and reach the detector 123 are adjusted based on the positioning of panels 151-154.

In a another further aspect, the collection NA is adjusted to effectively block particular grating anomaly singularities from reaching the detector by blocking specific area of the collection NA. In some examples, Wood's anomalies arise in particular, small ranges in {AOI, Az} space. Thus, in some embodiments, as depicted in FIG. 1, computing system 130 communicates a command signal 144 indicative of a desired collection NA to collection pupil 120. In response, programmable collection pupil 120 adjusts a state of the programmable collection pupil to block particular ranges of AOI and Az.

In some examples, two pairs of knife edges or slits may be located across the collection pupil plane to select particular ranges of AOI and Az, and effectively block grating anomaly singularities from reaching the detector. In another example, a programmable 2D MEMS device may be employed to block a grating anomaly singularity at the collection pupil by selectively absorbing particular ranges of AOI and Az, or selectively redirecting light associated with particular ranges of AOI and Az such that the redirected light is not incident on the detector.

Exemplary techniques for configuring the illumination and collection NA are described in detail in U.S. Pat. No. 9,228,943 issued on Jan. 5, 2016, assigned to KLA-Tencor Corporation, the contents of which are incorporated herein by reference in their entirety.

In another further aspect, the dimension of illumination field stop projected on the wafer plane is adjusted to optimize the resulting measurement accuracy and speed based on the nature of the target under measurement.

In some examples, the illumination field stop projected on the wafer plane is adjusted to shape the PSF to underfill the metrology target to reduce the impact of boundary conditions on grating anomalies.

In the embodiment depicted in FIG. 1, computing system 130 is configured to receive signals 125 indicative of the spectral response detected by CCD 123. Computing system 130 is further configured to determine control signals 142 that are communicated to programmable illumination field stop 112. Programmable illumination field stop 112 receives control signals 142 and adjusts the size of the illumination aperture to achieve the desired illumination field size.

In some examples, the illumination field stop is adjusted to optimize measurement accuracy and speed. In another example, the illumination field stop is adjusted to prevent image clipping by the spectrometer slit and corresponding degradation of measurement results. In this manner, the illumination field size is adjusted such that the image of the measurement target underfills the spectrometer slit. In one example, the illumination field stop is adjusted such that the projection of the polarizer slit of the illumination optics underfills the spectrometer slit of the metrology system.

In block 204, measurements of the periodic metrology target are performed with the metrology system based on the measurement recipe.

In another further aspect, measurements are improved by incorporating the optical system model at arbitrary Az angles to correct scatterometer signal errors introduced by the non-ideal polarization response of illumination and collection optics. These effects are significant at Az angles other than 0 and 90 degrees.

In one example, the mirrors incorporated in the illumination and collection arms of the optics system introduce signal errors. To minimize the impact of these errors, an optics model that includes these mirror effects is included as part of the regression of the measurement model. In some examples, the effect of non-ideal mirror behavior is calibrated out of the spectral signals before measurement analysis. This approach may be advantageous to not only improve measurement accuracy, but also address tool-to-tool matching.

As described herein any normal incidence or oblique incidence broadband optical metrology system may be configured to minimize sensitivity to grating anomalies. Exemplary measurement techniques that may be configured as described herein include, but are not limited to spectroscopic ellipsometry (SE), including Mueller matrix ellipsometry, rotating polarizer SE, rotating polarizer, rotating compensator SE, rotating compensator, rotating compensator, SE, spectroscopic reflectometry (SR), including polarized SR, unpolarized SR, spectroscopic scatterometry, scatterometry overlay, beam profile reflectometry, both angle-resolved and polarization-resolved, beam profile ellipsometry, single or multiple discrete wavelength ellipsometry, x-ray relectivity (XRR), x-ray fluorescence (XRF), grazing incidence x-ray fluorescence (GIXRF), x-ray ellipsometry, etc. In general, any metrology technique that includes illumination having multiple wavelengths may be contemplated, individually, or in any combination. For example, any SR or SE technique applicable to the characterization of semiconductor structures, including image based metrology techniques, may be contemplated, individually, or in any combination.

In a further embodiment, system 100 includes one or more computing systems 130 employed to perform measurements of actual device structures based on spectroscopic measurement data collected in accordance with the methods described herein. The one or more computing systems 130 may be communicatively coupled to the spectrometer (e.g., spectrometer 123). In one aspect, the one or more computing systems 130 are configured to receive measurement data 125 associated with measurements of the structure of specimen 115.

It should be recognized that one or more steps described throughout the present disclosure may be carried out by a single computer system 130 or, alternatively, a multiple computer system 130. Moreover, different subsystems of the system 100, such as the spectroscopic ellipsometer 123, may include a computer system suitable for carrying out at least a portion of the steps described herein. Therefore, the aforementioned description should not be interpreted as a limitation on the present invention but merely an illustration.

In addition, the computer system 130 may be communicatively coupled to the spectrometer 123 in any manner known in the art. For example, the one or more computing systems 130 may be coupled to computing systems associated with the spectrometer 123. In another example, the spectrometer 123 may be controlled directly by a single computer system coupled to computer system 130.

The computer system 130 of the metrology system 100 may be configured to receive and/or acquire data or information from the subsystems of the system (e.g., spectrometer 123 and the like) by a transmission medium that may include wireline and/or wireless portions. In this manner, the transmission medium may serve as a data link between the computer system 130 and other subsystems of the system 100.

Computer system 130 of metrology system 100 may be configured to receive and/or acquire data or information (e.g., measurement results, modeling inputs, modeling results, reference measurement results, etc.) from other systems by a transmission medium that may include wireline and/or wireless portions. In this manner, the transmission medium may serve as a data link between the computer system 130 and other systems (e.g., memory on-board metrology system 100, external memory, or other external systems). For example, the computing system 130 may be configured to receive measurement data from a storage medium (i.e., memory 132 or an external memory) via a data link. For instance, spectral results obtained using spectrometer 123 may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a measurement model or an actual device parameter value determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 5, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some examples, the measurement models are implemented as an element of a SpectraShape® optical critical-dimension metrology system available from KLA-Tencor Corporation, Milpitas, Calif., USA. In this manner, the model is created and ready for use immediately after the spectra are collected by the system.

In some other examples, the measurement models are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

In yet another aspect, the measurement model results described herein can be used to provide active feedback to a process tool (e.g., lithography tool, etch tool, deposition tool, etc.). For example, values of measured parameters determined based on measurement methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values and a trained measurement model may be communicated to a lithography tool, etch tool, or deposition tool.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the methods described herein.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
    an illumination source configured to generate an amount of illumination light at a plurality of wavelengths;
    an illumination optics subsystem configured to direct the amount of illumination light from the illumination source to a periodic metrology target disposed on a specimen under measurement at a plurality of available values of angle of incidence, azimuth angle, polarization state, or any combination thereof;
    a detector having a planar, two-dimensional surface sensitive to incident light, wherein the detector is configured to generate a plurality of output signals indicative of a response of the specimen to the amount of illumination light;
    a collection optics subsystem configured to collect an amount of collected light from the specimen and direct the amount of collected light to the surface of the detector; and
    a computing system configured to:
        determine a measurement model of a spectral response of the periodic metrology target to measurement by the metrology system at the plurality of available values of the angle of incidence, azimuth angle, illumination wavelength, polarization state, or any combination thereof;
        select a subset of the plurality of available values of the angle of incidence, azimuth angle, illumination wavelength, polarization state, or any combination thereof that reduces the presence of grating anomalies in a spectral response of the periodic metrology target to measurement by the metrology system at the selected subset of the plurality of available values; and
        generate a measurement recipe for a measurement of the periodic metrology target at the selected subset of the plurality of available values.

2. The metrology system of claim 1, wherein the selecting the subset of the available values involves an optimization of the measurement model for measurement precision, measurement sensitivity to parameters of interest, measurement accuracy, system matching to a metrology reference, computational effort, or any combination thereof.

3. The metrology system of claim 1, wherein the measurement model includes a model of the geometric and material properties of the metrology target.

4. The metrology system of claim 3, wherein the measurement model includes an optical model of the metrology system.

5. The metrology system of claim 1, wherein the metrology system includes a configurable collection pupil, and wherein the configurable collection pupil is adjusted to block light rays associated with a subset of the available values of the angle of incidence and azimuth angle in accordance with the measurement recipe.

6. The metrology system of claim 1, wherein the metrology system includes a configurable illumination pupil and wherein the configurable illumination pupil is adjusted to transmit a subset of the available values of the angle of incidence in accordance with the measurement recipe.

7. The metrology system of claim 1, wherein the metrology system includes a selectable polarizer element and a rotating compensator element, and wherein the selectable polarizer element is configured to generate a subset of the available values of the polarization state in accordance with the measurement recipe.

8. The metrology system of claim 1, wherein the metrology system is configured as any one or more of a spectroscopic ellipsometer and a spectroscopic reflectometer.

9. The metrology system of claim 1, wherein the amount of illumination light is broadband illumination light including a range of wavelengths spanning at least 500 nanometers.

10. The metrology system of claim 1, wherein an illumination spot size projected onto a surface of the specimen is smaller than a size of the periodic metrology target.

11. A method comprising:
    determining a measurement model of a spectral response of a periodic metrology target to measurement by a metrology system at a plurality of available values of an angle of incidence, azimuth angle, illumination wavelength, polarization state, or any combination thereof;
    selecting a subset of the plurality of available values of an angle of incidence, azimuth angle, illumination wavelength, polarization state, or any combination thereof that reduces the presence of grating anomalies in a spectral response of the periodic metrology target to measurement by the metrology system at the selected subset of the plurality of available values;
    generating a measurement recipe for a measurement of the periodic metrology target at the selected subset of the plurality of available values; and
    performing measurements of the periodic metrology target with the metrology system based on the measurement recipe.

12. The method of claim 11, wherein the selecting the subset of the available values involves an optimization of the measurement model for measurement precision, measurement sensitivity to parameters of interest, measurement accuracy, system matching to a metrology reference, computational effort, or any combination thereof.

13. The method of claim 11, wherein the measurement model includes a model of the geometric and material properties of the metrology target.

14. The method of claim 13, wherein the measurement model includes an optical model of the metrology system.

15. The method of claim 11, wherein the metrology system includes a configurable collection pupil, and wherein the configurable collection pupil is adjusted to transmit a subset of the available values of the angle of incidence and azimuth angle in accordance with the measurement recipe.

16. The method of claim 11, wherein the metrology system includes a configurable illumination pupil and wherein the configurable illumination pupil is adjusted to transmit a subset of the available values of the angle of incidence in accordance with the measurement recipe.

17. The method of claim 11, wherein the metrology system includes a selectable polarizer element and a rotating compensator element, and wherein the selectable polarizer element is configured to generate a subset of the available values of the polarization state in accordance with the measurement recipe.

18. A metrology system comprising:
an illumination source configured to generate an amount of illumination light at a plurality of wavelengths;
an illumination optics subsystem configured to direct the amount of illumination light from the illumination source to a periodic metrology target disposed on a specimen under measurement at a plurality of available values of angle of incidence, azimuth angle, polarization state, or any combination thereof;
a detector having a planar, two-dimensional surface sensitive to incident light, wherein the detector is configured to generate a plurality of output signals indicative of a response of the specimen to the amount of illumination light;
a collection optics subsystem configured to collect an amount of collected light from the specimen and direct the amount of collected light to the surface of the detector; and
a non-transitory, computer-readable medium, comprising:
code for causing a computing system to determine a measurement model of a spectral response of the periodic metrology target to measurement by the metrology system at the plurality of available values of the angle of incidence, azimuth angle, illumination wavelength, polarization state, or any combination thereof;
code for causing the computing system to select a subset of the plurality of available values of the angle of incidence, azimuth angle, illumination wavelength, polarization state, or any combination thereof that reduces the presence of grating anomalies in a spectral response of the periodic metrology target to measurement by the metrology system at the selected subset of the plurality of available values; and
code for causing the computing system to generate a measurement recipe for a measurement of the periodic metrology target at the selected subset of the plurality of available values.

19. The metrology system of claim 18, wherein the selecting the subset of the available values involves an optimization of the measurement model for measurement precision, measurement sensitivity to parameters of interest, measurement accuracy, system matching to a metrology reference, computational effort, or any combination thereof.

20. The metrology system of claim 18, wherein the metrology system includes a configurable collection pupil, and wherein the configurable collection pupil is adjusted to block light rays associated with a subset of the available values of the angle of incidence and azimuth angle in accordance with the measurement recipe.

* * * * *